(12) United States Patent
Ivey

(10) Patent No.: US 9,635,887 B2
(45) Date of Patent: May 2, 2017

(54) VAPOR DISPENSER SYSTEM

(71) Applicant: Johnathan Ivey, Chandler, AZ (US)

(72) Inventor: Johnathan Ivey, Chandler, AZ (US)

( * ) Notice: Subject to any disclaimer, the term of this patent is extended or adjusted under 35 U.S.C. 154(b) by 352 days.

(21) Appl. No.: 14/231,981

(22) Filed: Apr. 1, 2014

(65) Prior Publication Data

US 2014/0290650 A1 Oct. 2, 2014

Related U.S. Application Data

(60) Provisional application No. 61/807,428, filed on Apr. 2, 2013.

(51) Int. Cl.
*A24F 47/00* (2006.01)
*A61L 9/03* (2006.01)
*A61L 9/12* (2006.01)

(52) U.S. Cl.
CPC ............ *A24F 47/008* (2013.01); *A61L 9/03* (2013.01); *A61L 9/122* (2013.01); *A24F 47/00* (2013.01); *A24F 47/002* (2013.01); *A24F 47/004* (2013.01)

(58) Field of Classification Search
CPC ...... A24F 47/00; A24F 47/002; A24F 47/004; A24F 47/008; A61L 9/015; A61L 9/02; A61L 9/03; A61L 9/032; A61L 9/035; A61L 9/037; A61L 9/122; A61M 15/06
USPC ........... 128/202.21; 131/194, 270, 273, 329, 131/330; 290/1 R; 392/392, 404; 222/3, 222/146.5
See application file for complete search history.

(56) References Cited

U.S. PATENT DOCUMENTS

| | | | |
|---|---|---|---|
| 4,166,087 A * | 8/1979 | Cline | A61L 9/122 239/56 |
| 4,735,217 A | 4/1988 | Gerth et al. | |
| 4,922,901 A | 5/1990 | Brooks et al. | |
| 4,947,875 A | 8/1990 | Brooks et al. | |
| 5,060,671 A | 10/1991 | Counts et al. | |
| 8,314,591 B2 | 11/2012 | Terry et al. | |
| 8,757,170 B2 * | 6/2014 | Kaplani | A24F 1/30 131/194 |
| 2006/0196518 A1 | 9/2006 | Hon | |
| 2009/0283103 A1 | 11/2009 | Nielsen et al. | |

(Continued)

OTHER PUBLICATIONS http_www.volcanovaporizer; all.
molecular-mi; p. 20.

*Primary Examiner* — Lynne Anderson
*Assistant Examiner* — Elliot S Ruddie
(74) *Attorney, Agent, or Firm* — Keith L. Jenkins, Registered Patent Attorney, LLC; Keith L. Jenkins

(57) ABSTRACT

A handheld vapor dispenser with rapidly interchangeable vapor tubes extending outside of the dispenser housing. A first exemplary embodiment uses a battery and a timing circuit to volatize the vapor-producing material and a positive air pressure source, such as a squeeze bulb, to expel the vapor from the tube. A second exemplary embodiment is rechargeable and has multiple vapor tubes in parallel spaced-apart proximity extending from the housing. A recharging station for multiple vapor dispensers that also provides vapor tube storage and access is disclosed. A third exemplary embodiment couples positive air pressure to the air inlet of an electronic cigarette to expel vapor from the mouthpiece for flavoring drinks. A dispensing tube that sealingly attaches to the mouthpiece is also disclosed. Additional embodiments are disclosed.

11 Claims, 16 Drawing Sheets

(56) References Cited

U.S. PATENT DOCUMENTS

2011/0030706 A1 2/2011 Gibson et al.
2011/0120482 A1 5/2011 Brenneise

* cited by examiner

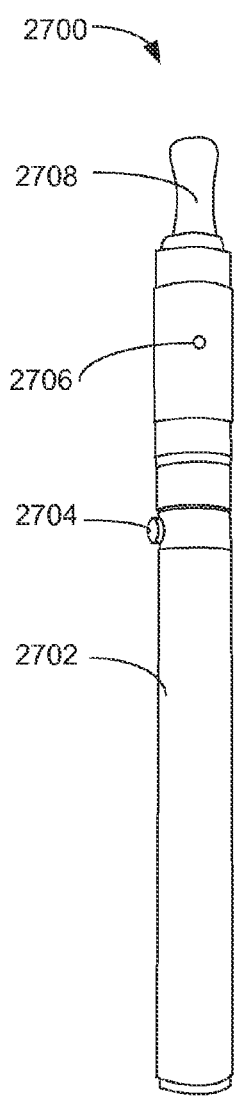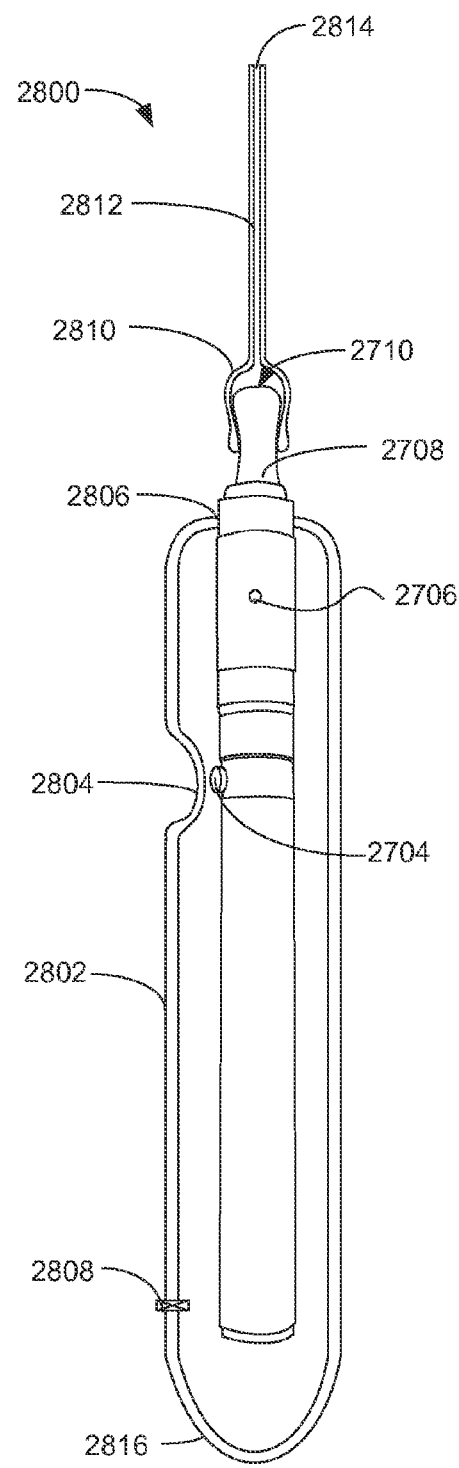
FIG. 27
PRIOR ART
FIG. 28

VAPOR DISPENSER SYSTEM

RELATED APPLICATIONS

This application claims the benefit of U.S. provisional patent application Ser. No. 61/807,428 filed Apr. 2, 2013 to at least one common inventor, the contents of which are hereby incorporated herein by reference.

TECHNICAL FIELD

This invention relates to providing a vapor dispensing system for dispensing flavored and/or scented vapors into beverages. In particular, this invention relates to providing a handheld vapor-dispenser unit with interchangeable flavor/scent tubes.

BACKGROUND

With the evolution of electronic cigarettes, it has been found that flavored and drugged vapors can be substituted for cigarette smoke, to avoid harmful tars and cyanides while providing a suction-based nicotine delivery system. Flavored vapors have progressed into the food service industry for providing scented vapors served over food to enhance the dining experience. Flavored vapors have also been added to beverages by percolating the flavored vapor into the beverage. Existing devices for this purpose are table top models that generate a large volume of vapor but which cannot change vapor flavors quickly.

Expired U.S. Pat. No. 4,922,901 discloses a puff-activated drug delivery system having a disposable air-permeable, battery-powered, resistance heated tubular member that contains an aerosol-forming material and a non-disposable portion that contains a battery, a puff-actuated current actuation means, and a regulator for the heater. Expired U.S. Pat. No. 4,947,875 discloses a puff-activated flavor delivery system similar to U.S. Pat. No. 4,922,901 except that the emphasis is on producing a flavored aerosol for direct oral use.

U.S. Pat. No. 8,314,591 discloses a charging case for a personal vaporizing inhaler. U.S. Pat. No. 8,314,591 discloses a personal vaporizer with two conductive surfaces that activates the vaporizer when both are touched (lips and hand). The two conductive surfaces can also be used to recharge the battery. The material to be vaporized is contained in a replaceable cartridge that is punctured to conduct the liquid contents to a wick near a heating element. A microprocessor is employed to detect when the cartridge is empty. A rechargeable battery-powered recharging cradle for one or two personal vaporizing units is provided.

US Published Patent Application 20110120482 discloses the use of a fan to blow air at a constant rate through a heater and through a solid vaporizable material to provide vapor to a mouthpiece.

A vaporizer for flavoring food is disclosed at www.volcanovaporizer which shows a tabletop vaporizer that produces scented or flavored vapor that is captured in a plastic bag and dispensed from the bag for various purposes. The material to be vaporized has to be prepared and loaded into the device. Cleaning appears to be required when changing flavors.

Therefore, a need exists for a handheld vaporizer that enables changing flavors quickly. A need also exists for a handheld vaporizer that can provide combinations of flavors quickly. A need also exists for a handheld vaporizer that propels the vapor out, rather than relying on suction. A need also exists for a handheld vaporizer that can be easily used by a bartender or other user to directly flavor drinks. A need also exists for a base station for one or more handheld vaporizers that includes electrical recharging and also provides easy-access storage for flavor tubes.

OBJECTS AND FEATURES OF THE INVENTION

A primary object and feature of the present invention is to overcome the above-mentioned problems and fulfill the above-mentioned needs.

Another object and feature of the present invention is to provide a system that can dispense vapors from a handheld unit. It is a further object and feature of the present invention to provide a system that enables rapid changes in the flavor of vapors to be dispensed. It is a further object and feature of the present invention to provide a system that enables multiple flavors of vapors to be dispensed concurrently. It is a further object and feature of the present invention to provide a system that takes up little countertop space for storage and recharging. It is a further object and feature of the present invention to be useful for flavoring beverages.

It is an additional primary object and feature of the present invention to provide such a system that is efficient, inexpensive and handy. Other objects and features of this invention will become apparent with reference to the following descriptions.

SUMMARY OF THE INVENTION

The apparatus of the present invention provides a system that can dispense vapors from a handheld unit. The system comprises apparatus for making rapid changes in the flavor of vapors to be dispensed. The system may also include a system that enables multiple flavors of vapors to be dispensed concurrently. The system also provides a system that takes up little countertop space for storage and recharging. The system is also useful for flavoring beverages.

More particularly, the invention includes a vapor dispenser, including a collar for releasably supporting respective a flavor tube; a power source for providing volatilizing energy to the flavor tube when the flavor tube is installed in the collar; a fluidic coupling between a positive air pressure source and the collar; and a housing configured to support the collar, the power source, and the fluidic coupling, where the housing is further sized and configured to be handheld. The vapor dispenser, where the flavor tube is supported to extend outside the housing. The vapor dispenser, where the positive air pressure source includes a squeeze bulb. The vapor dispenser, where the positive air pressure source includes a squeeze bulb and a one-way valve. The vapor dispenser, where the positive air pressure source includes a squeeze bulb extending at least partially outside the housing. The vapor dispenser, where the positive air pressure source includes a fluidic coupling to an air inlet of an electronic cigarette. The vapor dispenser, further including a dispensing tube extending from a resilient coupling adapted to sealingly fit onto a mouth piece of the electronic cigarette. The vapor dispenser, where the positive air pressure source includes a squeeze bulb and a one-way valve. The vapor dispenser, where the collar includes a resilient collar operable to frictionally and releasably retain respective a flavor tube. The vapor dispenser, where the positive air pressure source includes a fan. The vapor dispenser, where the collar includes first, second, and third collars arranged to releasably support respective first, second, and third interchangeable flavor tubes in parallel spaced apart proximity. The vapor dispenser, including first, second, and third automatic closures operable to independently close respective first, second, and third collars to fluid flow when no flavor tube is installed. The vapor dispenser, where the power source includes a rechargeable battery and a recharging station. The vapor dispenser, where the recharging station is configured to concurrently recharge a first plurality of the vapor dispensers and to support a second plurality of interchangeable flavor tubes.

Additional embodiments include a vapor dispenser, including one or more resilient collars operable to frictionally receive, releasably retain, and support respective flavor tubes; a power source coupled to provide volatilizing energy to the flavor tube when the flavor tube is installed in the collar; a fluidic coupling between a positive air pressure source and the collar; and a housing configured to support the collar, the power source, the fluidic coupling, and the positive air pressure source, where the housing is further configured to be handheld. The vapor dispenser, where the flavor tube is supported to extend outside the housing. The vapor dispenser, where the positive air pressure source includes a one-way valve through a squeeze bulb extending at least partially outside the housing or a fan. The vapor dispenser, further including an electronic cigarette; a squeeze bulb fluidically coupled to an air inlet of the electronic cigarette; a one-way valve through the squeeze bulb; and a dispensing tube extending from a resilient coupling adapted to sealingly fit onto a mouth piece of the electronic cigarette. The vapor dispenser, where: the collar includes first, second, and third collars arranged to releasably support respective first, second, and third interchangeable flavor tubes in parallel spaced apart proximity; first, second, and third automatic closures operable to independently close respective first, second, and third collars to fluid flow when no flavor tube is installed; and the power source includes a rechargeable battery and a recharging station configured to concurrently recharge a first plurality of the vapor dispensers and to support a second plurality of interchangeable flavor tubes. \

A final embodiment includes a vapor dispenser, including one or more resilient collars operable to frictionally receive, releasably retain, and support respective flavor tubes; a power source for providing volatilizing energy to the flavor tube when the flavor tube is installed in the collar; a fluidic coupling between a positive air pressure source and the collar; and a housing configured to support the collar, the power source, and the fluidic coupling, where the housing is further configured to be handheld and the collar supports the respective flavor tube to extend outside the housing; where the positive air pressure source includes a one-way valve through a squeeze bulb extending at least partially outside the housing or a fan; and where the vapor dispenser further includes an electronic cigarette, where the positive air pressure source includes a squeeze bulb fluidically coupled to an air inlet of the electronic cigarette; a one-way valve through the squeeze bulb; and a dispensing tube extending from either a resilient coupling adapted to sealingly fit onto a mouth piece of the electronic cigarette or the squeeze bulb; the one or more collars, including first, second, and third collars arranged to releasably support respective first, second, and third interchangeable flavor tubes in parallel spaced apart proximity; first, second, and third automatic closures operable to independently close respective first, second, and third collars to fluid flow when no flavor tube is installed; and the power source includes a rechargeable battery and a recharging station configured to concurrently recharge a first plurality of the vapor dispensers and to support a second plurality of interchangeable flavor tubes.

BRIEF DESCRIPTION OF THE DRAWINGS

The present invention will hereinafter be described in conjunction with the following drawing figures, wherein like numerals denote like elements.

FIG. 27 is a side elevation view illustrating a prior art oral vapor dispenser; and FIG. 28 is a side elevation view illustrating the prior art oral vapor dispenser of FIG. 27 with a cross-sectional view of a third exemplary embodiment of a vapor dispenser.

DETAILED DESCRIPTION OF THE PRESENT INVENTION

The term "flavor tube" as defined and used herein refers to an annular tube having between its inner and outer circumferential walls a heater, a supply of flavored material that can be vaporized with heat from the heater, and a vapor-permeable inner circumferential wall. Terms such as "bottom", "top", "right", "left" and other terms of relative location and orientation are defined relative to the particular drawing to which the description refers, and are not intended to imply that changes in orientation are limited. Like reference numbers on various figures refer to the same object. The hundreds digit(s) of each reference number refers to the number of the first figure in which the part is referenced.

Figure 1:
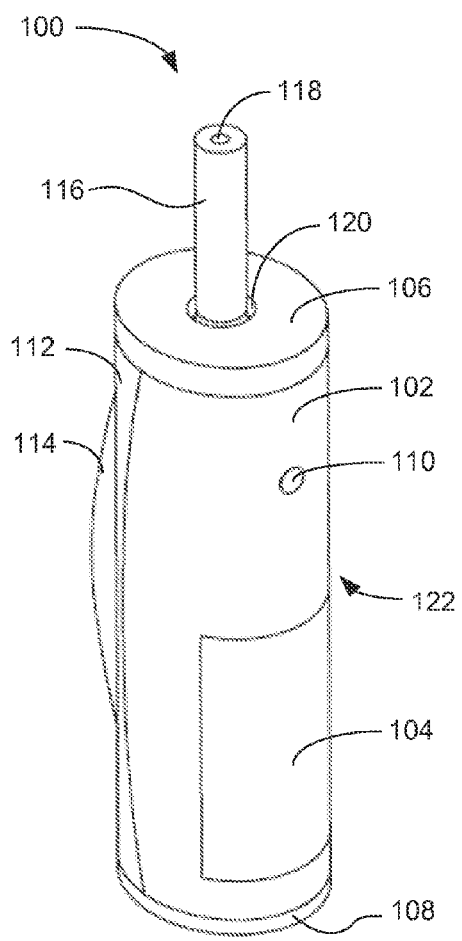
FIG. 1 is a top right front perspective view illustrating a first exemplary embodiment of the vapor dispenser, according to a preferred embodiment of the present invention.

FIG. 1 is a top right front perspective view illustrating a first exemplary embodiment of the vapor dispenser system 100, according to a preferred embodiment of the present invention. Vapor dispenser 100 includes a housing 122 that includes front housing panel 102, battery compartment cover 104, rear housing panel 112, top panel 106, and bottom panel 108. Housing 122 supports the positive air pressure source (illustrated as a squeeze bulb 114) and the collar 120 that supports flavor tube 116 to extend outside the housing 122. Front housing panel 102 receives and releasably retains battery compartment cover 104 and attaches to rear housing panel 112. Top panel 106 and bottom panel 108 attach to front housing panel 102 and rear housing panel 112 to complete the housing 122. Push button 110 extends from front housing panel 102. An exemplary fluid propulsion device 114, or positive air pressure source, illustrated as a resilient squeeze bulb 114, is mounted in the rear housing panel 112 of vapor dispenser 100 and extends partially outside the housing. Those of skill in the art, informed by the present disclosure, will appreciate the various fluid propulsion devices 114 that may be used in vapor dispenser system 100. Flavor tube 116 is resiliently received and releasably frictionally retained in resilient collar 120 of top panel 106. Flavor tube 116 has a hole 118 defined by the inner circumferential wall of flavor tube 116.

When electrical power is applied by using the pushbutton 110, a heating element within flavor tube 116 is activated vaporizing flavored material within the flavor tube 116 and allowing the vapors to be dispensed by a user squeezing squeeze bulb 114. One push of push button 110 provides about five seconds worth of heating, which is sufficient for producing enough vapor for flavoring one cocktail. Each flavor tube 116 preferably has sufficient flavor material for flavoring fifty cocktails. In operation, the top end of flavor tube 116 is inserted into the beverage and the vapor is squeezed into the beverage using the squeeze bulb 114. Part of the vapor dissolves in the beverage and part percolates to the surface and forms an attractive flavored and scented mist in the beverage glass above the beverage. In another operation, the vapor may be deposited into a beverage container on top of a beverage. In particular embodiments, the system may include covers, optionally disposable, for covering drink glasses to retain the vapor in the glass when being carried through the restaurant or bar by wait persons. Each flavor tube 116 can be easily and quickly manually removed and replaced with another flavor tube 116, to replace a depleted flavor tube 116 or to change flavors. In use in a bar room, speed is of the essence, as the many customers' various tastes must be accommodated in a timely manner.

Figure 2:
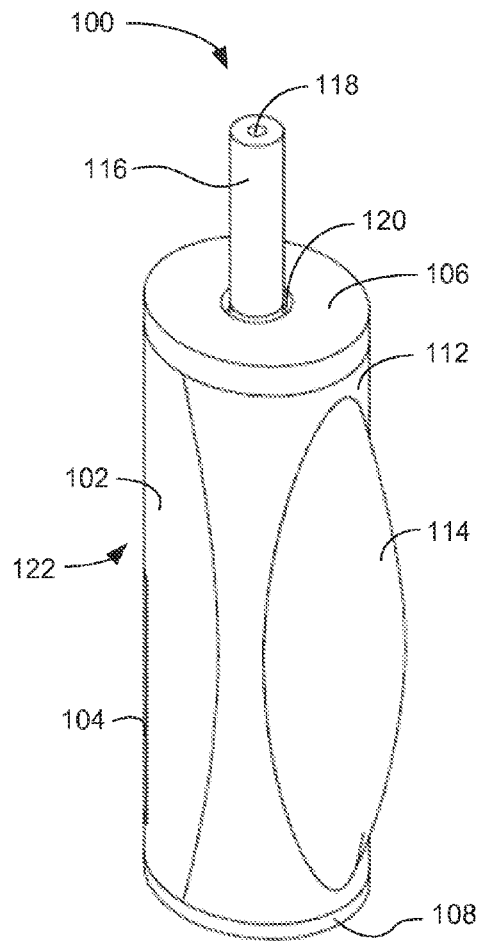
FIG. 2 is a top left rear perspective view illustrating the first exemplary embodiment of the vapor dispenser system of FIG. 1, according to a preferred embodiment of the present invention.

FIG. 2 is a top left rear perspective view illustrating the first exemplary embodiment of the vapor dispenser system 100 of FIG. 1, according to a preferred embodiment of the present invention. Squeeze bulb 114 and rear housing panel 112 can be more clearly seen in this view.

Figure 3:
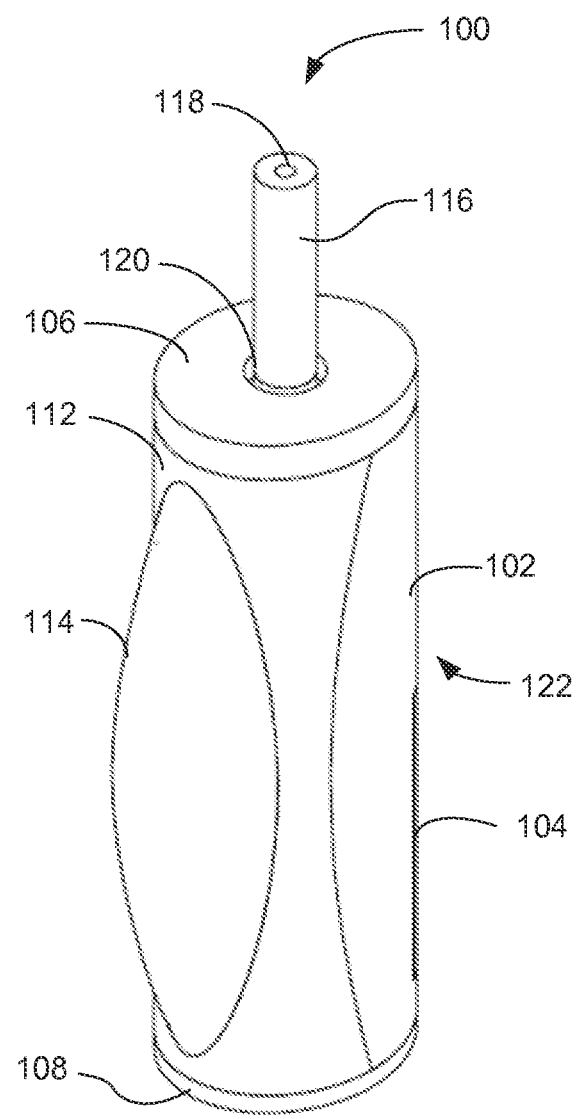
FIG. 3 is a top right rear perspective view illustrating the first exemplary embodiment of the vapor dispenser system of FIG. 1, according to a preferred embodiment of the present invention.

FIG. 3 is a top right rear perspective view illustrating the first exemplary embodiment of the vapor dispenser 100 of FIG. 1, according to a preferred embodiment of the present invention. In a particular embodiment, top plate 106 may accommodate more than one collar 120 and more than one flavor tube 116, and be wired to supply power to each.

Whether there are multiple or single collars 120, each collar preferably has an automatic closure for closing the opening of the collar 120 when no flavor tube 116 is installed. The automatic closure may be as simple as a spring-biased flapper valve that is pushed open when a flavor tube 116 is installed. Such valves are well known in the art and will not be further detailed here.

Figures 4, 5:
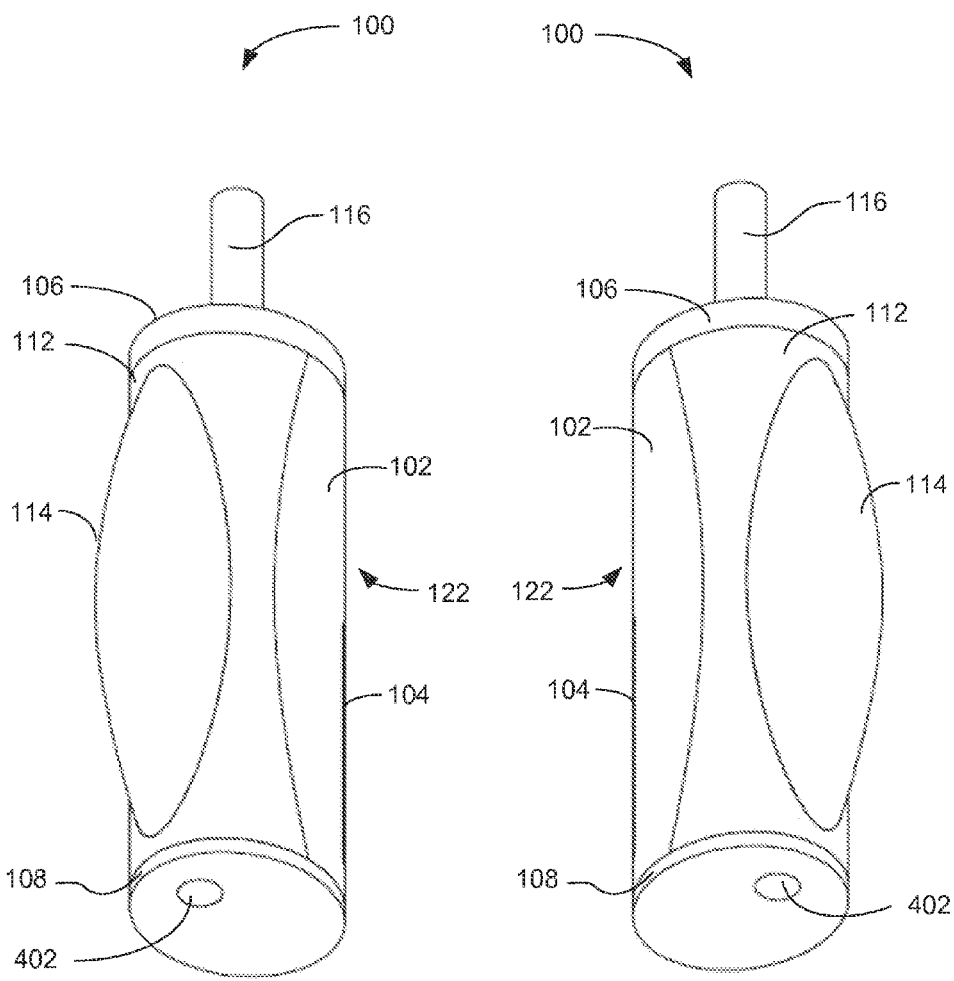
FIG. 4 is a bottom right rear perspective view illustrating the first exemplary embodiment of the vapor dispenser system of FIG. 1, according to a preferred embodiment of the present invention.
FIG. 5 is a bottom left rear perspective view illustrating the first exemplary embodiment of the vapor dispenser system of FIG. 1, according to a preferred embodiment of the present invention.

FIG. 4 is a bottom right rear perspective view illustrating the first exemplary embodiment of the vapor dispenser system 100 of FIG. 1, according to a preferred embodiment of the present invention. Inlet 402 in bottom plate 108 allows air into a one-way intake valve 606 (see FIG. 6) and further into chamber 624 (see FIG. 6) within the housing 122. The cross-sectional shape of the housing 122 is not a limitation of the invention. Various shapes, consistent with the constraint of being a handheld device, are within the scope of the present invention.

FIG. 5 is a bottom left rear perspective view illustrating the first exemplary embodiment of the vapor dispenser system 100 of FIG. 1, according to a preferred embodiment of the present invention. In various embodiments, inlet 402 may be of various shapes and sizes, and may be located in any functional and convenient place.

Figure 6:
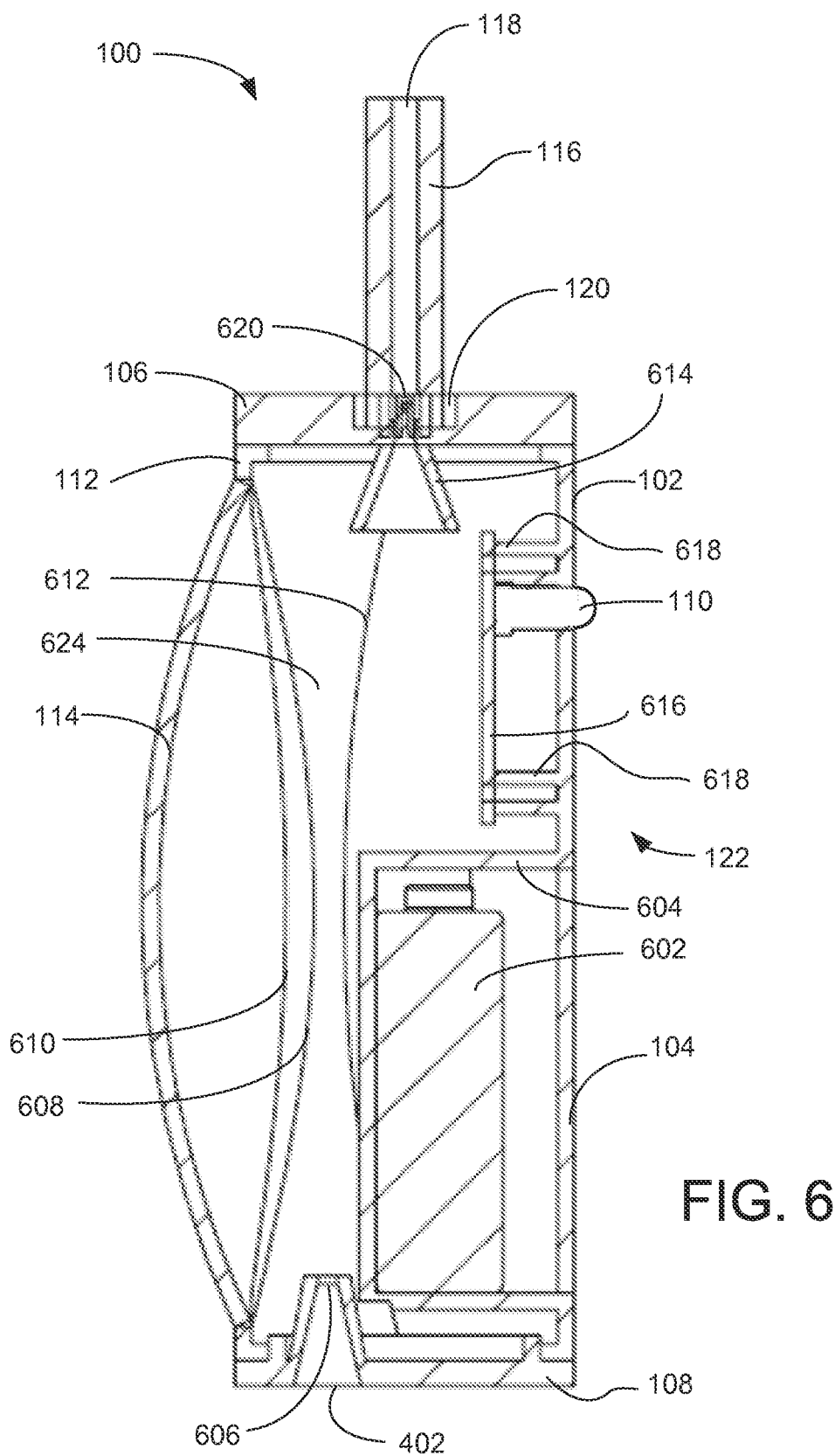
FIG. 6 is a cross-sectional side elevation view illustrating the first exemplary embodiment of the vapor dispenser system of FIG. 1, according to a preferred embodiment of the present invention.

FIG. 6 is a cross-sectional side elevation view illustrating the first exemplary embodiment of the vapor dispenser system 100 of FIG. 1, according to a preferred embodiment of the present invention. Power source 602, illustrated as battery 602, is releasably secured in battery compartment 604 behind battery compartment door 104. Battery 602 is preferably a replaceable battery 602. In various embodiments, battery 602 may be a rechargeable battery 602. Power source 602 provides energy for volatilizing the vapor-producing material within the flavor tube 116. Battery 602 is electrically connected to circuit board 616 which, in turn, is electrically connected to flavor tube 116. The wiring is not shown as it is known in the art and would needlessly complicate the drawing.

One-way intake valve 606 extends from the top of bottom plate 108 and opens to allow air into chamber 624 responsive to squeeze bulb 114 expanding resiliently after initially being compressed. One-way intake valve 606 works cooperatively with one-way exhaust valve 614 that extends from the underside of top plate 106. When one-way intake valve 606 is open, one-way exhaust valve 614 is closed, and vice versa, enabling air to first be forced out of chamber 624 through one-way exhaust valve 614 and hole 118 responsive to squeeze bulb 114 being compressed and then drawing air into chamber 624 responsive to squeeze bulb 114 expanding resiliently after initially being compressed. Aperture 620 accelerates the airflow out through the hole 118, thereby lowering the air pressure and entraining the heat-volatized vapor into the air stream. Edges 608 and 610 are cutaway edges of the rear housing panel 112 along the boundary with squeeze bulb 114, and do not form a boundary of chamber 624. Edge 612 is the boundary between rear housing panel 112 and front housing panel 102, and does not define a boundary of chamber 624.

Circuit board 616 is mounted on fastener receivers 618 and includes a switch (not shown) activated by push button 110. When the button is pushed, circuit board 616 switches power to the flavor tube 116 and initiates a counter that counts for five seconds before removing power from the flavor tube 116. The five second limit is used for portion control and limiting the temperature of the flavor tube 116.

Figure 7:
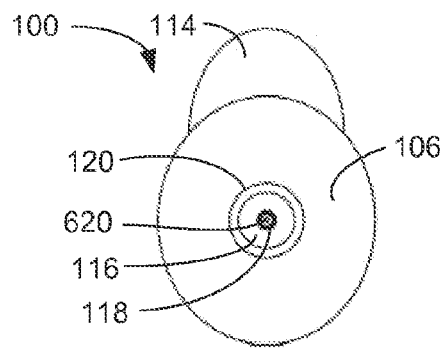
FIG. 7 is a top plan view illustrating the first exemplary embodiment of the vapor dispenser system of FIG. 1, according to a preferred embodiment of the present invention.

FIG. 7 is a top plan view illustrating the first exemplary embodiment of the vapor dispenser 100 system of FIG. 1, according to a preferred embodiment of the present invention. Aperture 620 can be seen centered at the bottom of hole 118 inside flavor tube 116 installed in collar 120 on elliptical top plate 106. Squeeze bulb 114 extends outward in an uncompressed state, as shown.

Figure 8:
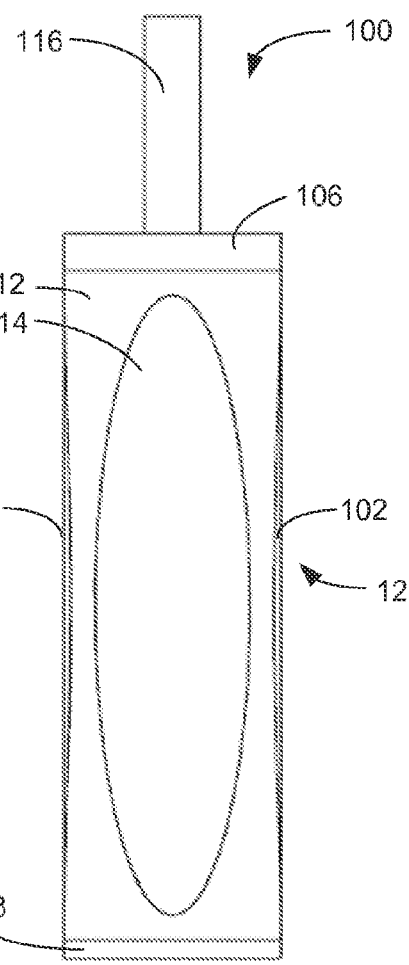
FIG. 8 is a rear elevation view illustrating the first exemplary embodiment of the vapor dispenser system of FIG. 1, according to a preferred embodiment of the present invention.

FIG. 8 is a rear elevation view illustrating the first exemplary embodiment of the vapor dispenser system 100 of FIG. 1, according to a preferred embodiment of the present invention. Rear housing panel 112 has a narrow middle portion, such that portions of front housing panel 102 can be seen in this view.

Figure 9:
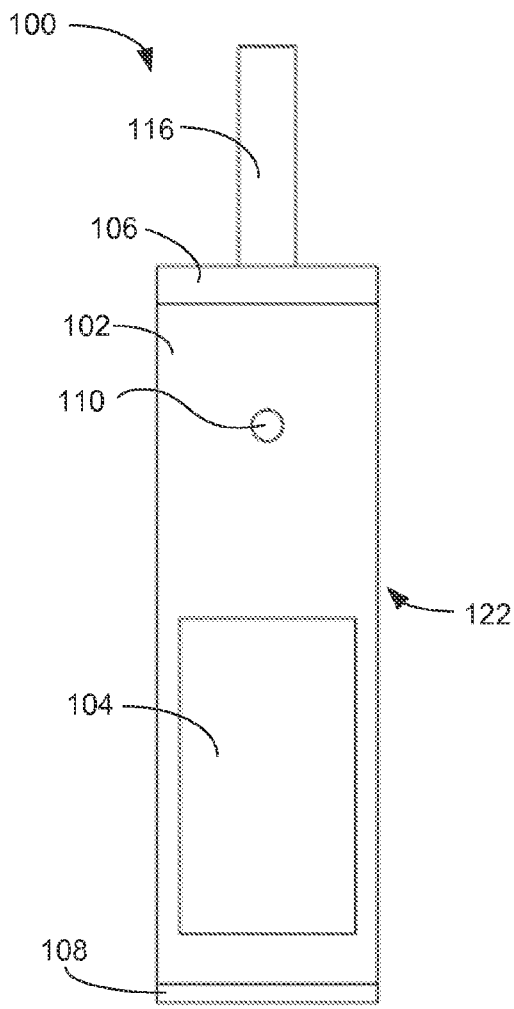
FIG. 9 is a front elevation view illustrating the first exemplary embodiment of the vapor dispenser system of FIG. 1, according to a preferred embodiment of the present invention.

FIG. 9 is a front elevation view illustrating the first exemplary embodiment of the vapor dispenser 100 system of FIG. 1, according to a preferred embodiment of the present invention. Battery compartment door 104 is shown as rectangular in this view. In various embodiments, various other shapes may be used, within the constraint of functioning as a battery compartment door.

Figure 10:
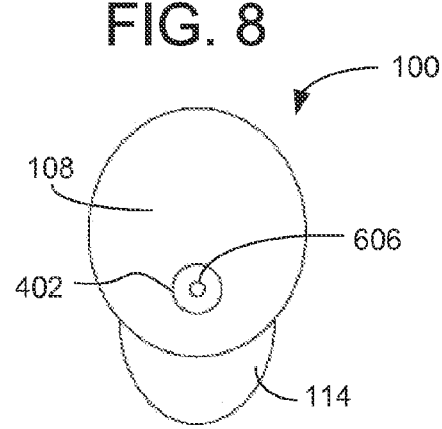
FIG. 10 is a bottom plan view illustrating the first exemplary embodiment of the vapor dispenser system of FIG. 1, according to a preferred embodiment of the present invention.

FIG. 10 is a bottom plan view illustrating the first exemplary embodiment of the vapor dispenser 100 system of FIG. 1, according to a preferred embodiment of the present invention. One-way intake valve 606 can be seen centered in inlet 402 on elliptical bottom plate 108. Squeeze bulb 114 extends outward in an uncompressed state, as shown.

Figure 11:
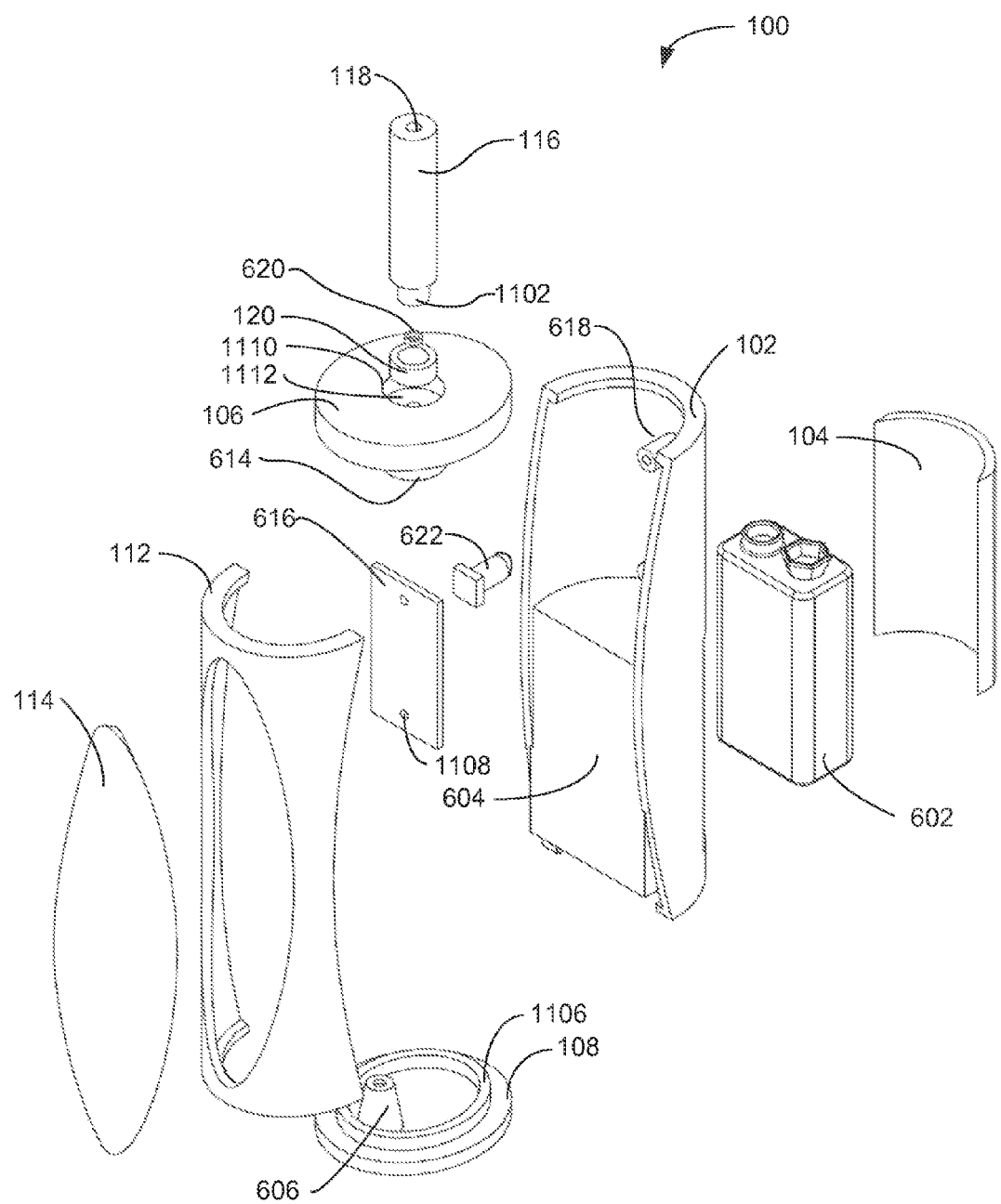
FIG. 11 is a right front perspective exploded view illustrating the first exemplary embodiment of the vapor dispenser system of FIG. 1, according to a preferred embodiment of the present invention.

FIG. 11 is a right front perspective exploded view illustrating the first exemplary embodiment of the vapor dispenser system 100 of FIG. 1, according to a preferred embodiment of the present invention. Flavor tube 116 has a bottom extension 1102 with a smaller diameter than the remainder of flavor tube 116. Bottom extension 1102 is the portion of flavor tube 116 sized and shaped to be received in collar 120. Thus, there is no preferred radial orientation for inserting flavor tube 116 into collar 120, making changing out flavor tubes 116 easier and quicker. Aperture 620 is fixed within a bottom portion of hole 118.

Bottom plate has an inner circumferential rim 1106 to assist in supporting rear housing panel 112 and front housing panel 102. Circuit board 616 has fastener openings 1108 (one of two labeled) for receiving fasteners that couple with fastener receivers 618.

Figure 12:
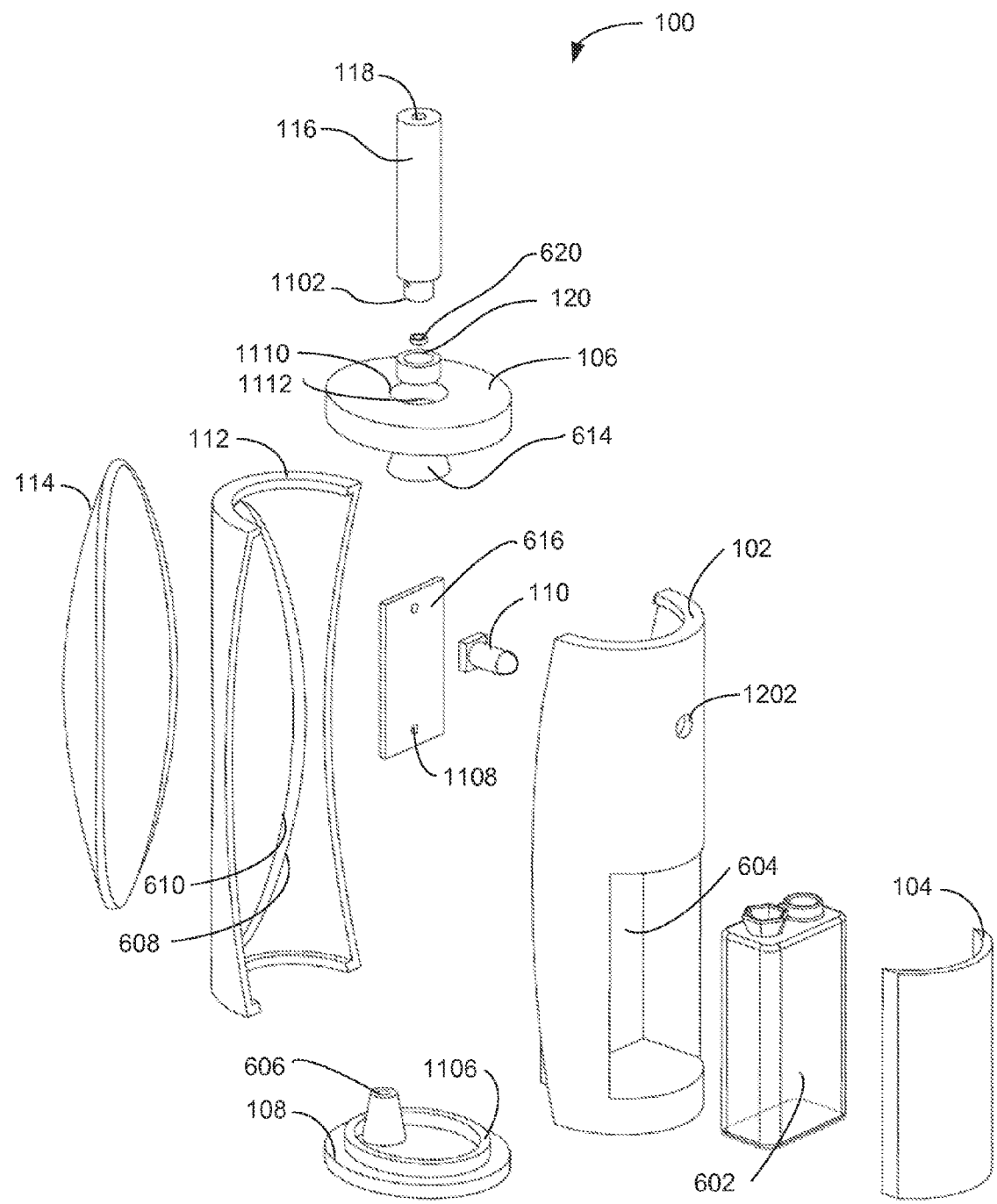
FIG. 12 is a right rear perspective exploded view illustrating the first exemplary embodiment of the vapor dispenser system of FIG. 1, according to a preferred embodiment of the present invention.

FIG. 12 is a right rear perspective exploded view illustrating the first exemplary embodiment of the vapor dispenser system 100 of FIG. 1, according to a preferred embodiment of the present invention. Opening 1202 in front housing panel 102 receives the pushbutton 110.

Figure 13:
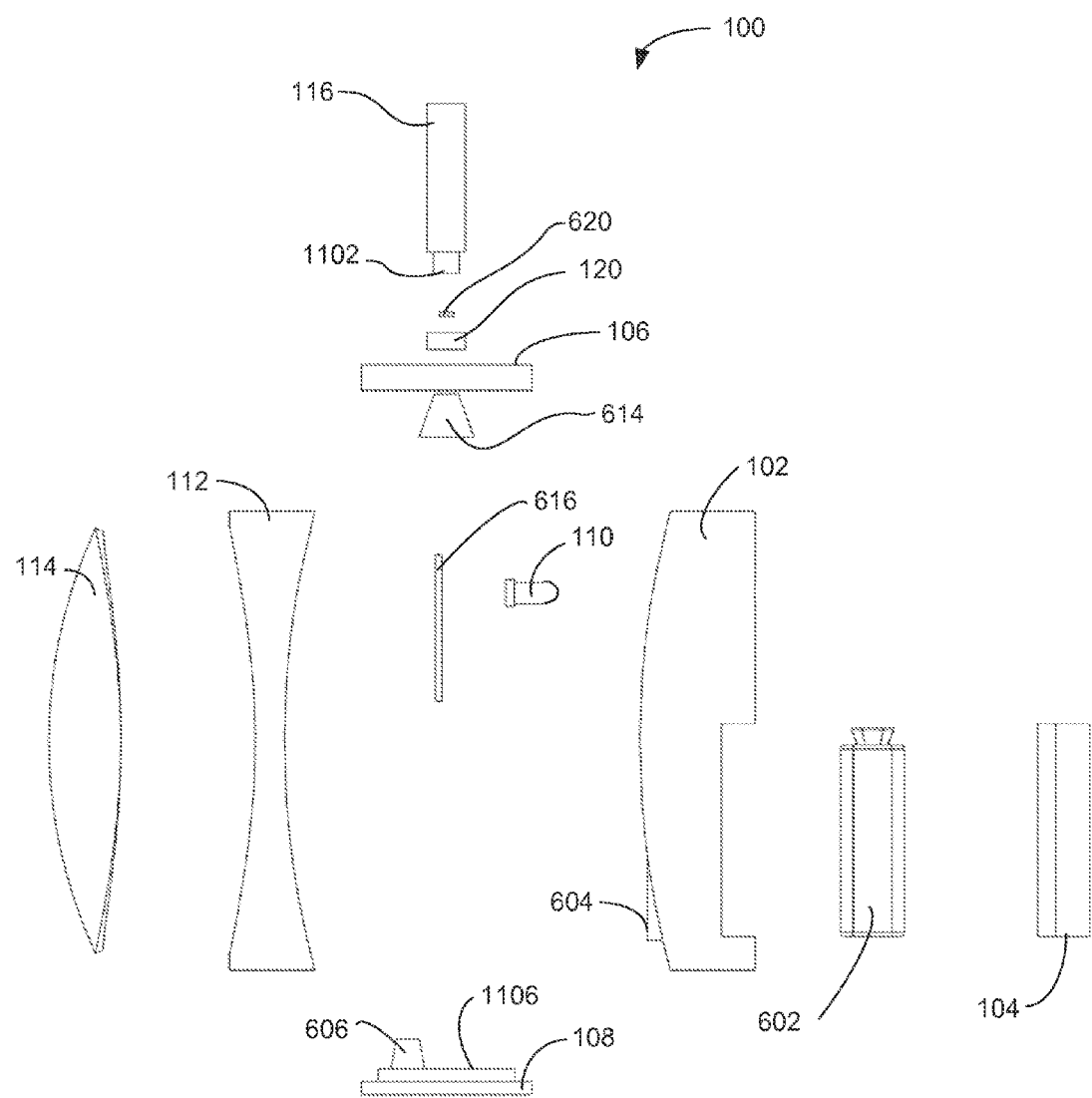
FIG. 13 is a side elevation exploded view illustrating the first exemplary embodiment of the vapor dispenser system of FIG. 1, according to a preferred embodiment of the present invention.

FIG. 13 is a side elevation exploded view illustrating the first exemplary embodiment of the vapor dispenser system 100 of FIG. 1, according to a preferred embodiment of the present invention. A rear portion of battery compartment 604 can be seen in this view.

Figure 14:
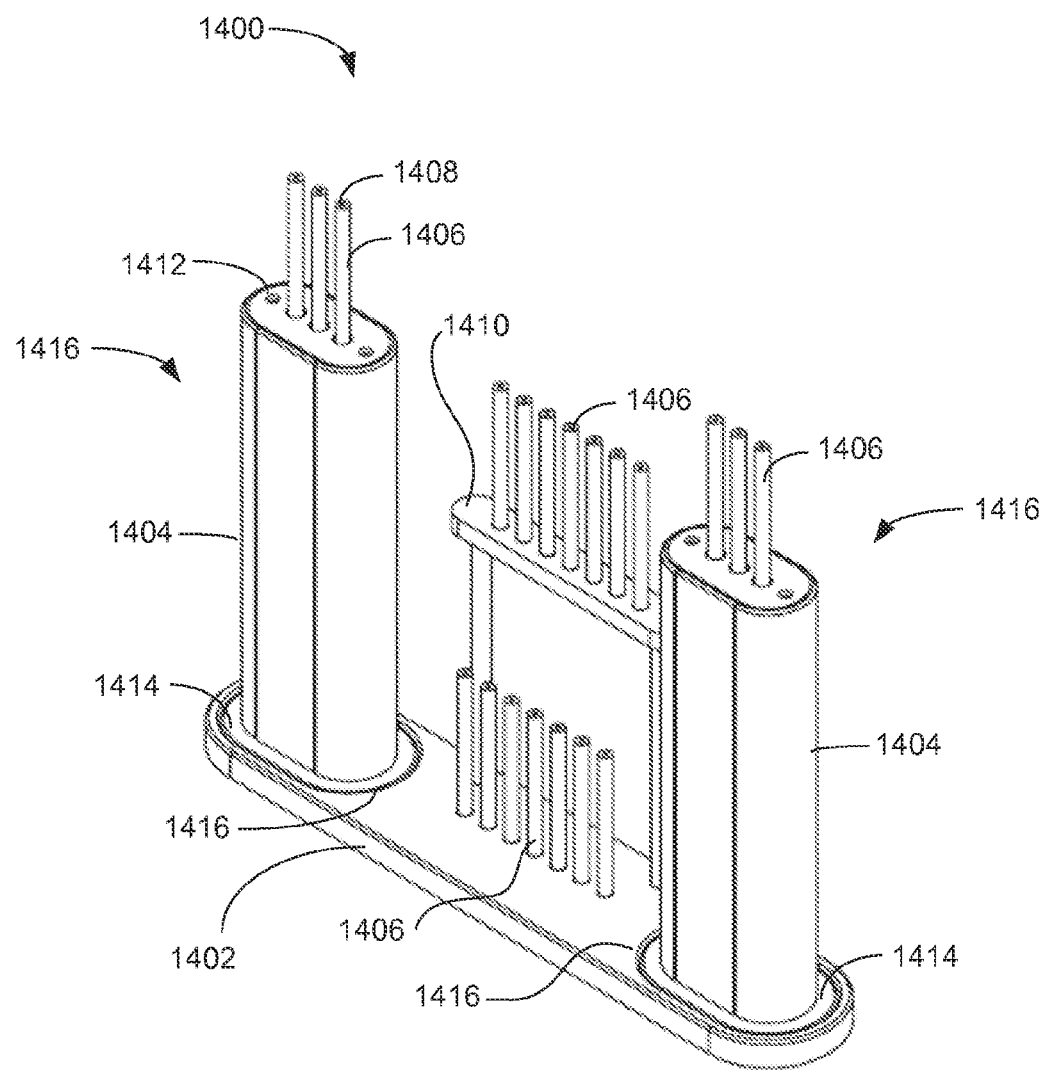
FIG. 14 is a top front perspective view illustrating the second exemplary embodiment of a vapor dispenser, according to a second preferred embodiment of the present invention.

FIG. 14 is a top front perspective view illustrating the second exemplary embodiment of a vapor dispenser system 1400, according to a second preferred embodiment of the present invention. Base 1402 supports two hand-held vapor dispensers 1416 in base sockets 1414. Hand-held vapor dispensers have base panels 1414 that fit in base sockets 1414 and support main housing 1404. Base sockets 1414 are recharging sockets for hand-held vapor dispensers 1416. Base 1402 also supports storage rack 1410, which supports a plurality of interchangeable flavor tubes 1406 (one of seven labeled). In addition, the base 1402 also directly supports another plurality of interchangeable flavor tubes 1406 (one of seven labeled). Each hand-held vapor dispenser 1416 has up to three flavor tubes 1406 fluidically coupled to a positive pressure air supply and electrically coupled to an electrical power supply. Flavor tubes 1406 are similar to flavor tubes 116, as previously discussed. The capacity for multiple flavor tubes 1406 enables simultaneous delivery of various flavored vapors. For example, a vodka cocktail could be simultaneously flavored with chocolate, cherry, and vanilla. Less than all three vapor tubes 1406 may be used at one time, as sockets 1926 (see FIG. 19) automatically close if no flavor tube 1406 is installed. Fastener openings 1412 assist in fastening each hand-held vapor dispenser 1416 together.

Figure 15:
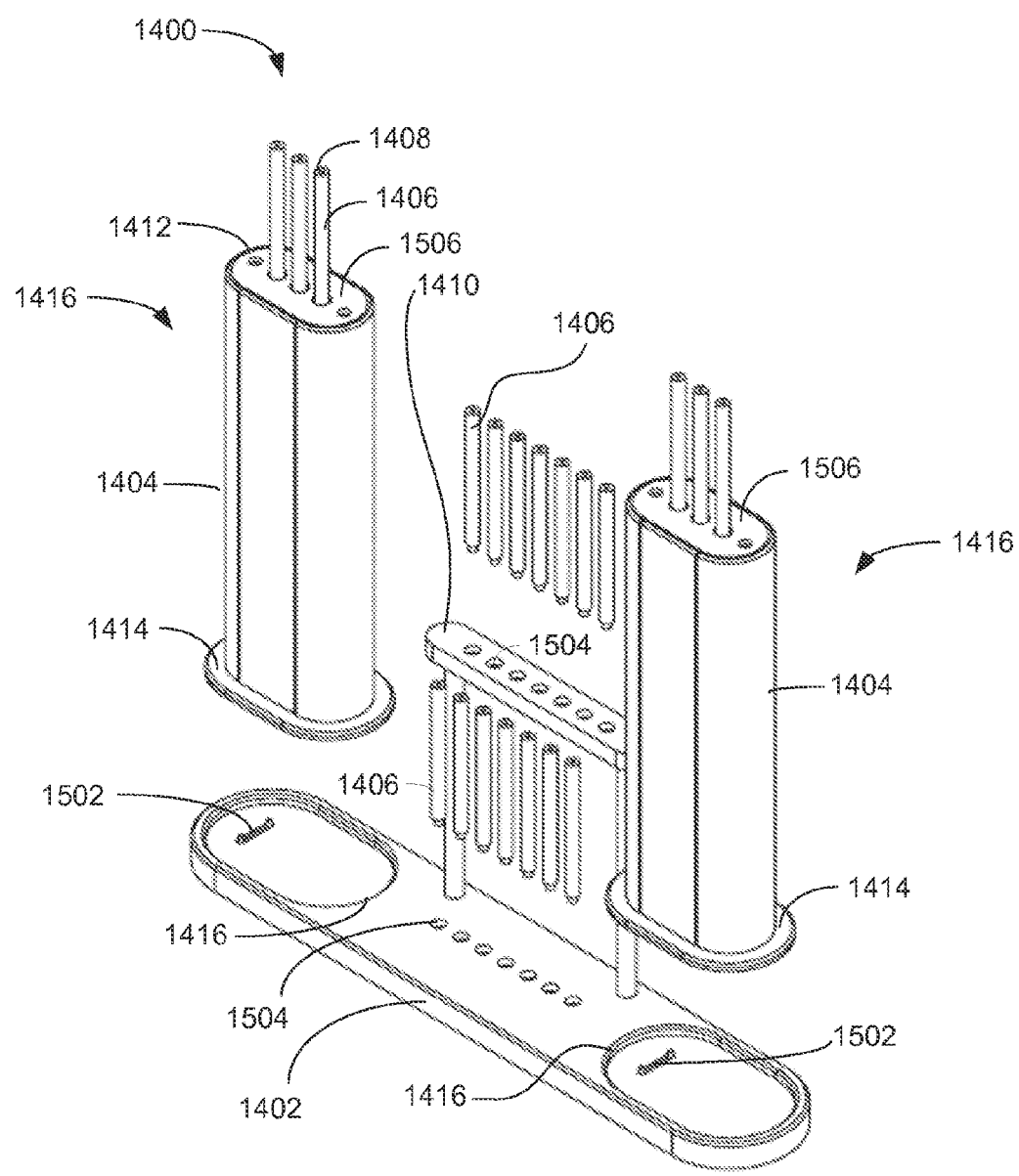
FIG. 15 is a top front perspective exploded view illustrating the second exemplary embodiment of the vapor dispenser system of FIG. 14, according to a second preferred embodiment of the present invention.

FIG. 15 is a top front perspective exploded view illustrating the second exemplary embodiment of the vapor dispenser system 1400 of FIG. 14, according to a second preferred embodiment of the present invention. Base electrical connectors 1502 couple to complimentary connectors in the base panels 1414 of each hand-held vapor dispenser 1416. An electrical power cord (not shown), extends from base 1402 to an external power supply (not shown) and provides power to base electrical connectors 1502. The power is used to recharge power storage within the handheld vapor dispenser 1416. Storage sockets 1504 resiliently receive, frictionally retain, and support flavor tubes 1406 in parallel, spaced apart proximity, as shown. In various additional embodiments, a base 1402 may support more than two hand-held vapor dispensers 1416. Top panels 1506 are secured through fastener openings 1412 and have three tube sockets, or collars, 1926 (see FIG. 19) each. In a particular embodiment, top panels 1506 may have more or fewer collars 1926.

Figure 16:
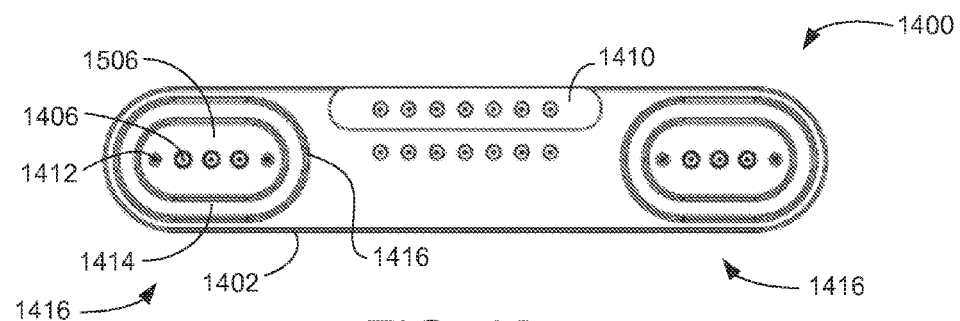
FIG. 16 is a top plan view illustrating the second exemplary embodiment of the vapor dispenser system of FIG. 14, according to a second preferred embodiment of the present invention.

FIG. 16 is a top plan view illustrating the second exemplary embodiment of the vapor dispenser system 1400 of FIG. 14, according to a second preferred embodiment of the present invention. The illustrated shapes of base 1402 and hand-held vapor dispensers 1416 are not limitations of the invention.

Figure 17:
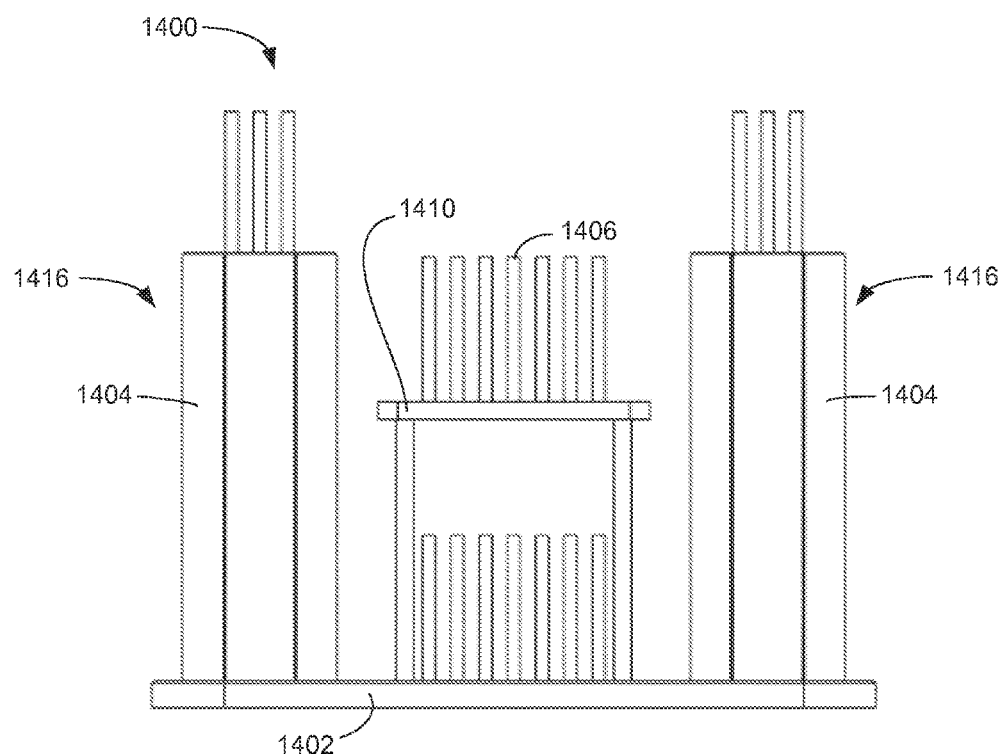
FIG. 17 is a front elevation view illustrating the second exemplary embodiment of the vapor dispenser system of FIG. 14, according to a second preferred embodiment of the present invention.

FIG. 17 is a front elevation view illustrating the second exemplary embodiment of the vapor dispenser system 1400 of FIG. 14, according to a second preferred embodiment of the present invention. The preferred spacing between flavor tubes 1406 is ergonomically determined to maximize ease of use. In addition, flavor tubes 1406 may be colored or otherwise marked to indicate the various flavors provided.

Figure 18:
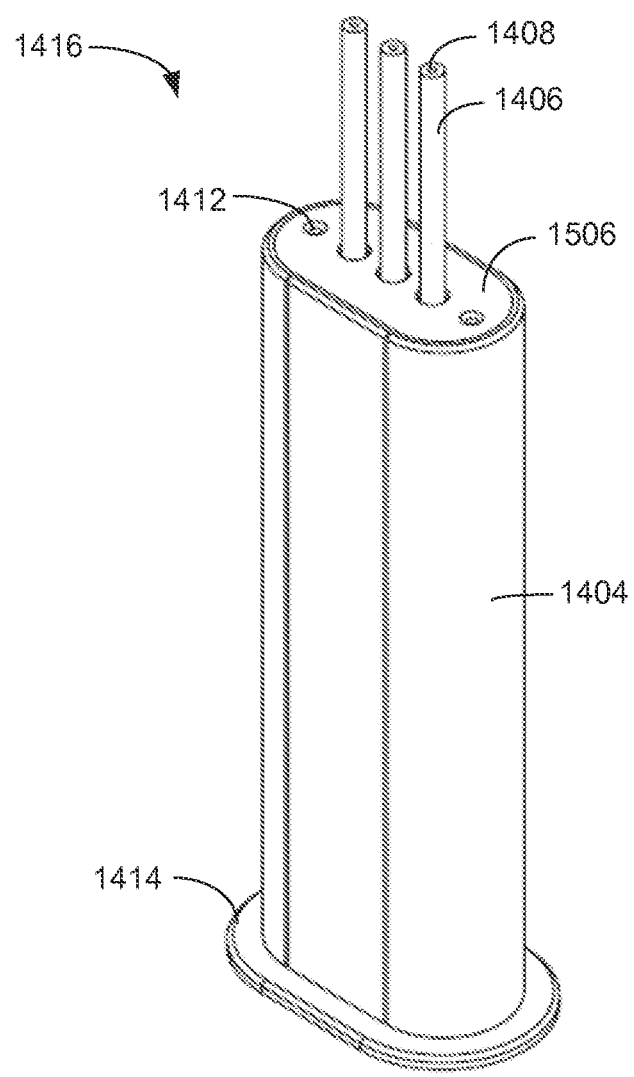
FIG. 18 is a top front perspective view illustrating the second exemplary handheld vapor dispenser of the second exemplary embodiment of the vapor dispenser system of FIG. 14, according to a second preferred embodiment of the present invention.

FIG. 18 is a top front perspective view illustrating a handheld vapor dispenser 1416 of the second exemplary embodiment of the vapor dispenser system 1400 of FIG. 14, according to a second preferred embodiment of the present invention. Housing 1404 is preferably plastic, but the invention is not so limited. Housing 1404 may be colored or have an emblem or design on the outer surface of housing 1404.

Figure 19:
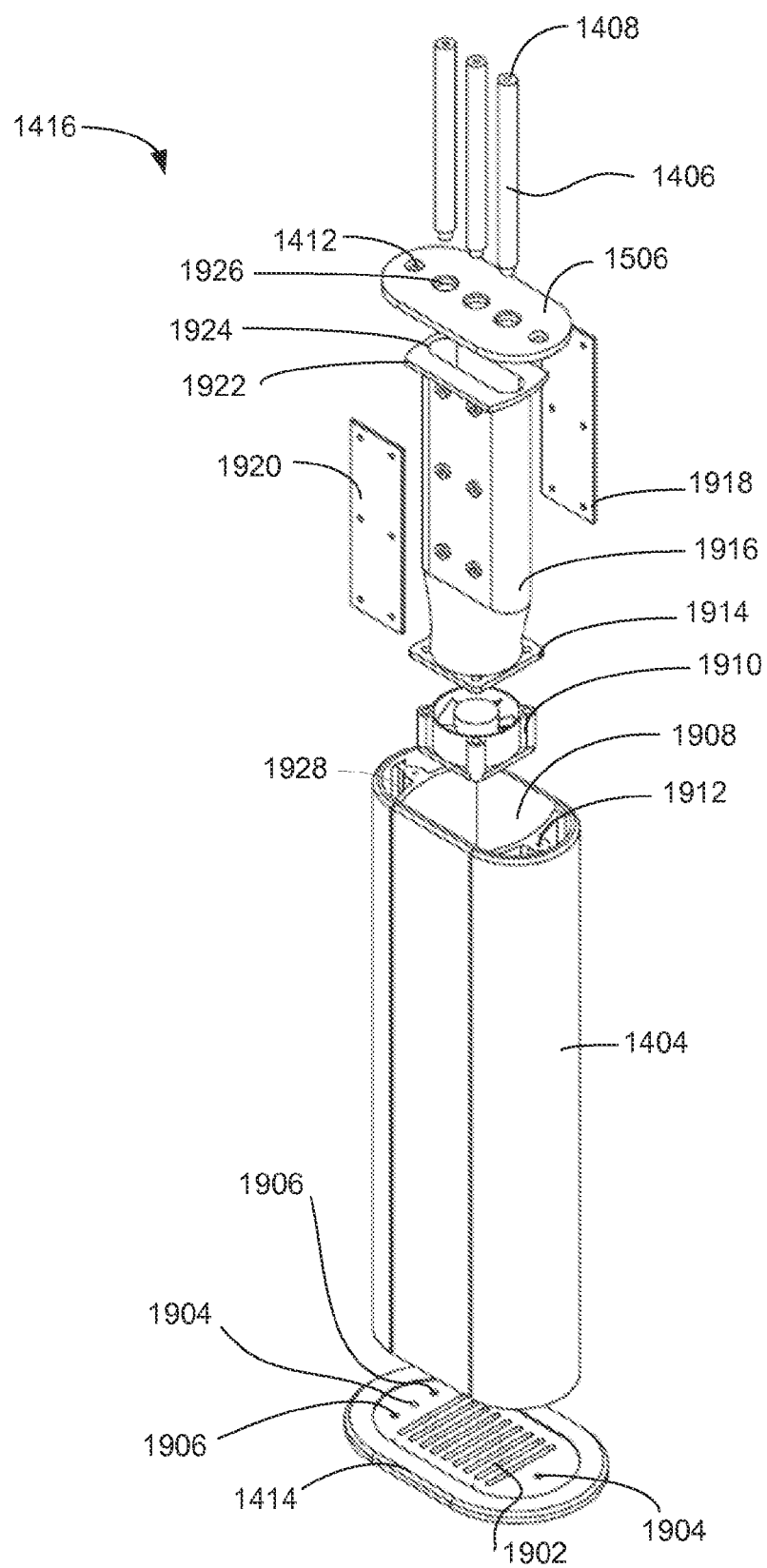
FIG. 19 is a top front perspective exploded view illustrating the second exemplary handheld vapor dispenser of the second exemplary embodiment of the vapor dispenser system of FIG. 14, according to a second preferred embodiment of the present invention.

FIG. 19 is a top front perspective exploded view illustrating a handheld vapor dispenser 1416 of the second exemplary embodiment of the vapor dispenser system 1400 of FIG. 14, according to a second preferred embodiment of the present invention. Base panel 1414 has an open grill 1902 to provide input air for the handheld vapor dispenser 1416. Base panel also has fastener holes 1904 for assisting in coupling base panel to housing 1404 and electrical contacts 1906 for conducting power from base electrical connectors 1502 for use within housing 1404. Housing 1404 is supported on base panel 1414 and fastened to base panel 1414 using fasteners assisted by fastener holes 1906. Housing 1404 has internal support ribs 1928 providing rib fastener holes 1912 and defining inner chamber 1908. Electrical fan 1910 rests on open grill 1902 in chamber 1908 and supports device 1916, which contains the power storage means and provides an air flow channel 1924. The power storage means is preferably a rechargeable battery, but that is not a limitation of the invention. Device 1916 has a bottom flange 1914 for coupling to fan 1910. Circuit boards 1920 and 1918 attach to the outside opposing surfaces of device 1916 and support circuits operable to control power and timing for vapor production. A five-second application of power to the flavor tubes 1406 may be initiated by a manual switch or, optionally, by lifting the handheld vapor dispenser 1416 out of base 1402. Device 1916 has a top flange 1922 which fits conformally into chamber 1908 and abuts top panel 1506 when installed. Top panel is fastened, via fastener openings 1412 and rib fastener holes 1912 to housing 1404. Sockets 1926 (one of three labeled) resiliently receive and frictionally retain flavor tubes 1406 and each socket 1926 automatically closes when no flavor tube 1406 is installed.

Figure 20:
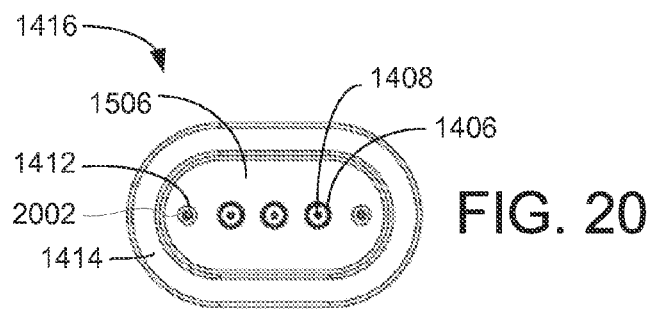
FIG. 20 is a top plan view illustrating the second exemplary handheld vapor dispenser of the second exemplary embodiment of the vapor dispenser system of FIG. 14, according to a second preferred embodiment of the present invention.

FIG. 20 is a top plan view illustrating a handheld vapor dispenser 1416 of the second exemplary embodiment of the vapor dispenser system 1400 of FIG. 14, according to a second preferred embodiment of the present invention. Fasteners 2002 (one of two labeled) can be seen in fastener openings 1412 (one of two labeled) in this view.

Figures 21, 22:
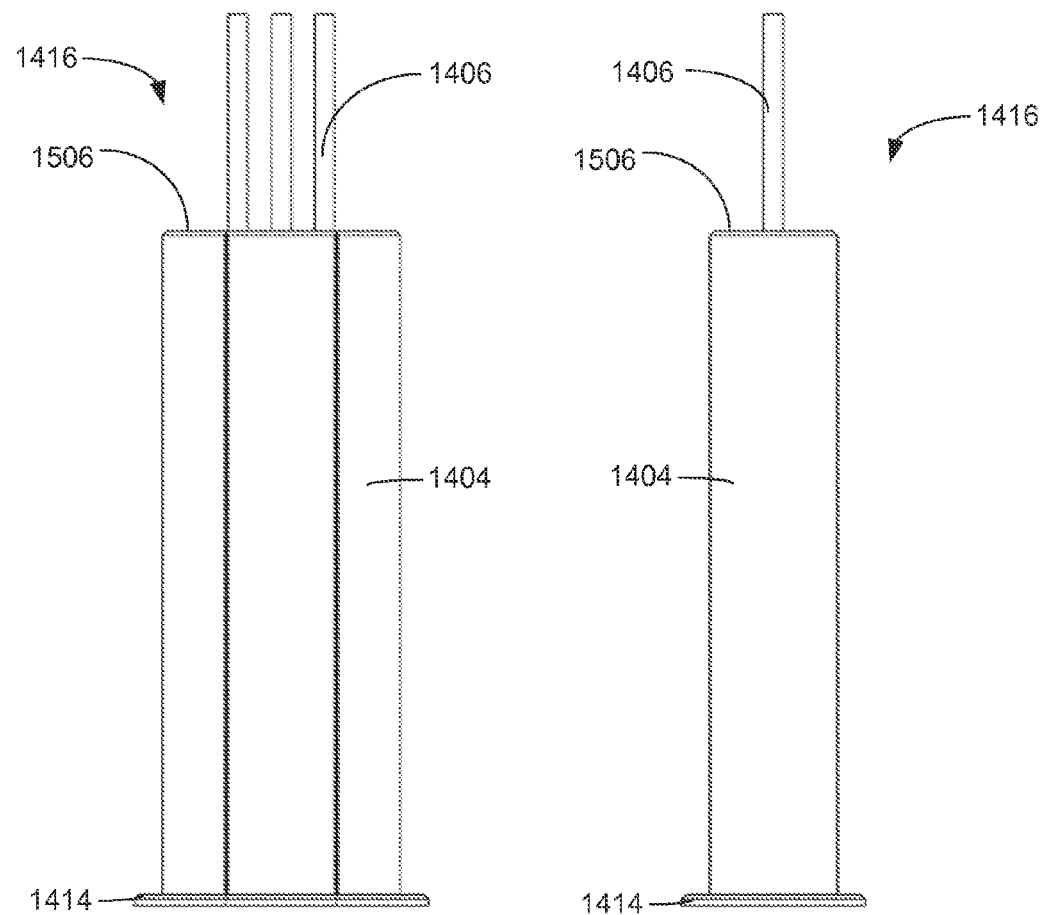
FIG. 21 is a front elevation view illustrating the second exemplary handheld vapor dispenser of the second exemplary embodiment of the vapor dispenser system of FIG. 14, according to a second preferred embodiment of the present invention.
FIG. 22 is a side elevation view illustrating the second exemplary handheld vapor dispenser of the second exemplary embodiment of the vapor dispenser system of FIG. 14, according to a second preferred embodiment of the present invention.

FIG. 21 is a front elevation view illustrating a handheld vapor dispenser 1416 of the second exemplary embodiment of the vapor dispenser system 1400 of FIG. 14, according to a second preferred embodiment of the present invention. Housing 1404 is preferably formed of injection molded plastic.

FIG. 22 is a side elevation view illustrating a handheld vapor dispenser 1416 of the second exemplary embodiment of the vapor dispenser system 1400 of FIG. 14, according to a second preferred embodiment of the present invention. Arrangement of the three flavor tubes 1406 is illustrated as being in a straight line, but the invention is not so limited. Any pattern may be used, within the constraint that all flavor tubes are in sufficient proximity to concurrently flavor the same beverage with vapor.

Figure 23:
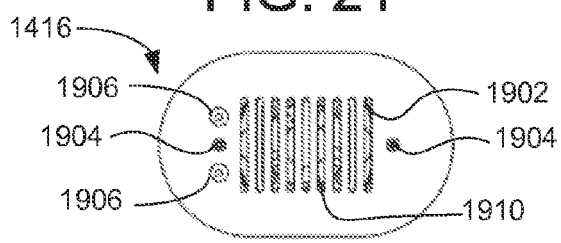
FIG. 23 is a bottom plan view illustrating the second exemplary handheld vapor dispenser of the second exemplary embodiment of the vapor dispenser system of FIG. 14, according to a second preferred embodiment of the present invention.

FIG. 23 is a bottom plan view illustrating a handheld vapor dispenser 1416 of the second exemplary embodiment of the vapor dispenser system 1400 of FIG. 14, according to a second preferred embodiment of the present invention. Fan 1910 can be seen behind open grill 1902 in this view.

Figure 24:
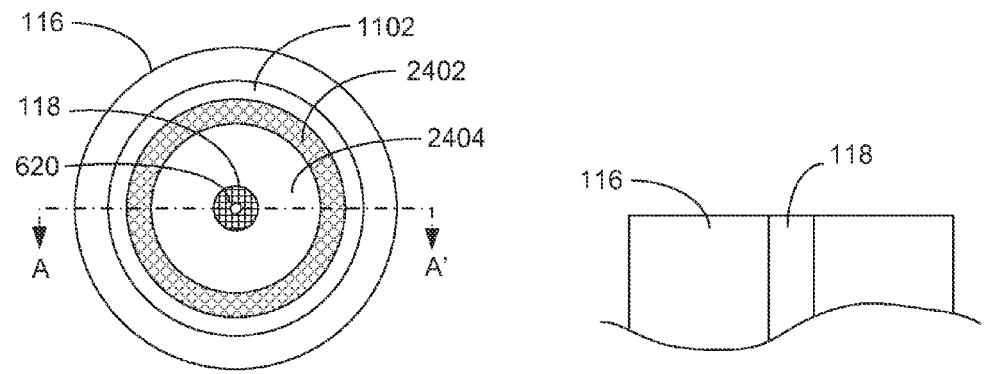
FIG. 24 is a bottom plan view illustrating an exemplary flavor tube of the second exemplary embodiment of the vapor dispenser system of FIG. 14 and defining cross section AA', according to a second preferred embodiment of the present invention.

FIG. 24 is a bottom plan view illustrating an exemplary flavor tube 116 and 1406 of the first and second exemplary embodiments of the vapor dispenser system 100 and 1400 of FIG. 1 and FIG. 14 and defining cross section AA', according to first and second preferred embodiments of the present invention. While the flavor tube 116 and 1406 is labeled for the first embodiment in the drawings of FIGS. 24-26, the drawings implicitly illustrate identical flavor tube 1406. Bottom extension 1102 is the negative electrode for conducting power to the heater within flavor tube 116. Insulator 2402 isolates positive electrode 2404 from bottom extension 1102. Hole 118 receives aperture 620, as previously described.

Figure 25:
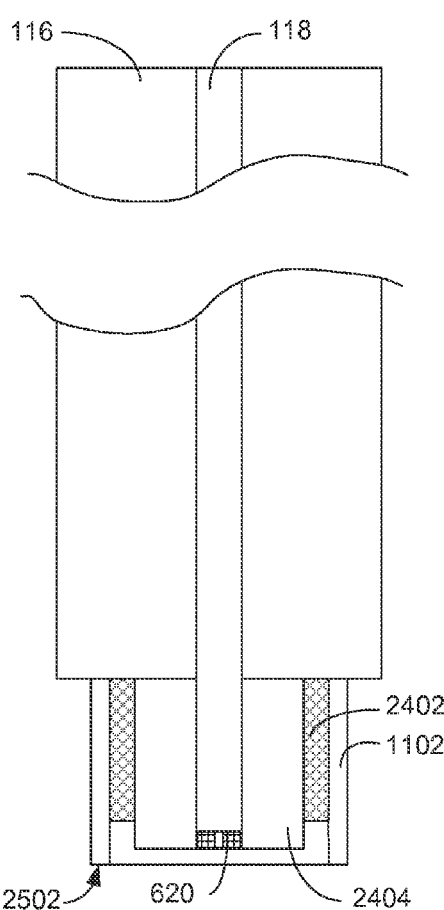
FIG. 25 is a cross sectional view through cross section AA' illustrating an exemplary flavor tube of the second exemplary embodiment of the vapor dispenser system of FIG. 14, according to a second preferred embodiment of the present invention.

FIG. 25 is a cross sectional view through cross section AA' illustrating an exemplary flavor tube 116 of the second exemplary embodiment of the vapor dispenser system 1400 of FIG. 14, according to a second preferred embodiment of the present invention. Positive electrode 2404 is recessed relative to a bottom surface 2502 of bottom extension 1102. Insulator 2402 does not fully cover positive electrode 2404 or bottom extension 1102.

Figure 26:
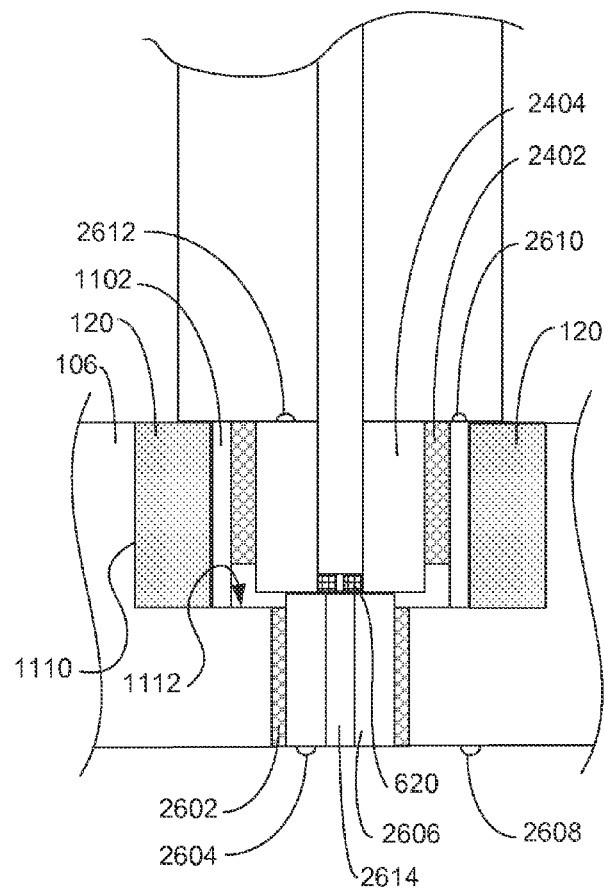
FIG. 26 is a cross sectional view through cross section AA' illustrating an exemplary flavor tube of the second exemplary embodiment of the vapor dispenser system of FIG. 14 installed in a socket, according to a second preferred embodiment of the present invention.

FIG. 26 is a cross sectional view through cross section AA' illustrating exemplary flavor tubes 116 and 1406 of the first and second exemplary embodiments of the vapor dispenser systems 100 and 1400 of FIG. 1 and FIG. 14 installed in a collar 120 in socket 1110, according to a first preferred embodiment of the present invention. Socket 1110 in top panel 106 retains collar 120 which, in turn, resiliently receives and frictionally retains bottom extension 1102. Top plate 106 has a conductor 2606 which is illustrated as an annular conductor around top plate bore 2614, but the annular shape of conductor 2606 is not a limitation of the invention. Conductor 2606 extends above the bottom surface 1112 of socket 1110 to contact positive electrode 2404 and is insulated from top panel 106 by an enclosing insulator 2602. Conductor 2606 has a first power supply wire contact 2604 for connecting a power supply wire to conductor 2606. Bottom extension 102 makes contact with bottom surface 1112 of socket 1110 and thereby, top panel 106. Top panel 106 has a second power supply wire contact 2608 for connecting a power supply wire to top panel 106 to provide power to bottom extension 1102, which serves as the negative electrode. Positive electrode 2404 has a first heater wire contact 2612 and bottom extension 1102 (negative electrode) has a second heater wire contact 2610 for coupling a heater within flavor tube 116 or 1406 to the electrodes 2404 and 1102.

FIG. 27 is a side elevation view illustrating a prior art oral vapor dispenser 2700. Oral vapor dispenser 2700, also known as an electronic cigarette 2700, includes a body 2702, a switch 2704, and air inlet 2706, a mouthpiece 2708, and a vapor outlet 2710. The Oral vapor dispenser 2700 may be, for example, an eGo C Twist manufactured by Joyetech™ and distributed through us.Joyetech.com. Air inlet 2706 is illustrated in exaggerated scale in order to make it visible in the drawing. Air inlet 2706 may be one of a plurality of air inlets 2706. The size of air inlets 2706 is kept small to create the drag that users expect when puffing on a cigarette. In operation, a user activates the switch 2704 (illustrated as a push-button switch 2704) to initiate vapor production within the oral vapor dispenser 2700 and then sucks on the mouthpiece to draw air into the dispenser 2700 through air inlet 2706 to entrain the vapor into the user's mouth.

FIG. 28 is a side elevation view illustrating the prior art oral vapor dispenser 2700 of FIG. 27 with a cross-sectional view of a third exemplary embodiment of a vapor dispenser 2800. Flexible, resilient, and generally cylindrical silicone squeeze bulb 2802 receives an oral vapor dispenser 2700 through resilient sealing opening 2806 and encloses at least the air inlet 2706. In the illustrated embodiment, squeeze bulb 2802 includes an adaptation 2804 for accessing the switch 2704. In various other embodiments, with this or various other oral vapor dispensers, the squeeze bulb 2802 may not cover the switch 2704. Squeeze bulb 2802 also includes a one-way inlet valve 2808, which allows air to enter the squeeze bulb 2800 as it resiliently recovers from being squeezed. While squeeze bulb 2802 is illustrated with an entire bottom end 2816, other embodiments may feature a bottom seal, similar to the resilient sealing opening 2806, that can sealingly engage the oral vapor dispenser 2700. In a preferred embodiment, the axial extent of the enclosure, whether by the squeeze bulb 2802 directly or by other means, for the oral vapor dispenser 2700 is reduced to allow for easy changing of vapor tubes within the oral vapor dispenser 2700, within the constraint of fluidically accessing the air inlet 2706.

In operation, the switch 2704 is activated and vapor is produced within the oral vapor dispenser 2700. Then the squeeze bulb 2802 is squeezed, forcing air into air inlet 2706 which entrains the vapor and forces the vapor/air mixture out the vapor outlet 2710 in mouthpiece 2708. Thus, the vapor may be deposited in a beverage container on top of a beverage in order to impart flavor and/or aroma to the beverage.

Vapor dispenser 2800 may optionally include dispensing tube 2812, which includes resilient sealing mouthpiece fitting 2810 and vent 2814. In operation, vapor exiting vapor outlet 2710 travels through dispensing tube 2812 and out vent 2814. Dispensing tube 2812 enables the user to dispense vapors into the beverage itself by inserting the dispensing tube 2812 into the beverage while dispensing vapor.

The illustrated third embodiment is merely exemplary, and not a limitation. Those of ordinary skill in the art, enlightened by the present disclosure, will appreciate that a wide variety of configurations for the third embodiment are within the scope of the invention. For non-limiting example, a loose sleeve extending from the bottom rim of the resilient sealing mouthpiece fitting 2810 and receiving only enough of the oral vapor dispenser 2700 to enclose the air inlet 2706 may have a resilient sealing end and a fluidic connection to a squeeze bulb having a one-way valve. Such a device could be installed over the mouthpiece end of the oral vapor dispenser 2700. Various embodiments that fluidically connect a positive air pressure source, exemplified as a squeeze bulb 2802, to the air inlet 2706 of an oral vapor dispenser 2700 are within the scope of the present invention.

Although applicant has described applicant's preferred embodiments of this invention, it will be understood that the broadest scope of this invention includes such modifications as diverse shapes and sizes and materials. Such scope is limited only as provided in the above specification and the claims below.

Further, many other advantages of applicant's invention will be apparent to those skilled in the art from the above descriptions.

I claim:

1. A vapor dispenser, comprising:
   a. at least one collar, contiguous with a housing, for releasably supporting respective at least one flavor tube;
   b. a power source for providing volatilizing energy to said at least one flavor tube when said at least one flavor tube is installed in said at least one collar;
   c. a fluidic coupling between a positive air pressure source and said at least one collar;
   d. said housing configured to support said power source, and said fluidic coupling, wherein said housing is further sized and configured to be handheld; and
   e. wherein said at least one collar comprises: first, second, and third collars arranged to releasably support respective first, second, and third interchangeable flavor tubes in parallel spaced apart proximity.

2. The vapor dispenser of claim 1, wherein said at least one flavor tube is supported to extend outside said housing.

3. The vapor dispenser of claim 1, wherein said at least one collar comprises a resilient collar operable to frictionally and releasably retain respective at least one flavor tube.

4. The vapor dispenser of claim 1, wherein said positive air pressure source comprises a fan.

5. The vapor dispenser of claim 1, comprising: only one flavor tube installed.

6. The vapor dispenser of claim 1, comprising: first, second, and third automatic closures operable to independently close respective first, second, and third collars to fluid flow when no flavor tube is installed.

7. The vapor dispenser of claim 4, wherein said power source comprises a rechargeable battery and a recharging station.

8. The vapor dispenser of claim 7, wherein said recharging station is configured to concurrently recharge a first plurality of said vapor dispensers and to support a second plurality of interchangeable flavor tubes.

9. A vapor dispenser, comprising:
a. at least one resilient collar, contiguous with a housing, operable to frictionally receive, releasably retain, and support respective at least one flavor tube;
b. a power source coupled to provide volatilizing energy to said at least one flavor tube when said at least one flavor tube is installed in said at least one collar;
c. a fluidic coupling between a positive air pressure source and said at least one collar;
d. said housing configured to support said power source, said fluidic coupling, and said positive air pressure source, wherein said housing is further configured to be handheld; and
e. wherein said at least one collar comprises: first, second, and third collars arranged to releasably support respective first, second, and third interchangeable flavor tubes in parallel spaced apart proximity.

10. The vapor dispenser of claim 9, wherein said at least one flavor tube is supported to extend outside said housing.

11. The vapor dispenser of claim 9, wherein:
a. said at least one collar comprises first, second, and third collars arranged to releasably support respective first, second, and third interchangeable flavor tubes in parallel spaced apart proximity;
b. first, second, and third automatic closures operable to independently close respective first, second, and third collars to fluid flow when no flavor tube is installed; and
c. said power source comprises a rechargeable battery and a recharging station configured to concurrently recharge a first plurality of said vapor dispensers and to support a second plurality of interchangeable flavor tubes.

* * * * *